US00PP26613P2

(12) United States Plant Patent
Wood

(10) Patent No.: US PP26,613 P2
(45) Date of Patent: Apr. 19, 2016

(54) ***SAMBUCUS* PLANT NAMED 'SMNSRD4'**

(50) Latin Name: *Sambucus racemosa*
Varietal Denomination: SMNSRD4

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 98 days.

(21) Appl. No.: 14/120,739

(22) Filed: Jun. 21, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Sambucus* plant named 'SMNSRD4', characterized by its compact, upright to outwardly spreading and mounded plant habit; vigorous growth habit; freely branching habit; dense and bushy habit; finely-dissected leaves that are bright yellow green in the spring and/or under full sunlight conditions and yellow green in the late summer and/or under partial shade conditions; leaves that are resistant to sun scalding; and good garden performance.

2 Drawing Sheets

Botanical designation: *Sambucus racemosa.*
Cultivar denomination: 'SMNSRD4'.

BACKGROUND OF THE INVENTION

The present invention relates to a new and distinct *Sambucus* plant, botanically known as *Sambucus racemosa* and hereinafter referred to by the name 'SMNSRD4'.

The new *Sambucus* plant is a product of a controlled breeding program conducted by the Inventor in Grand Haven, Mich. The objective of the breeding program is to create new *Sambucus* plants with attractive leaf color and sun-tolerance.

The new *Sambucus* plant originated from a cross-pollination in May, 2006 in Grand Haven, Mich. of *Sambucus racemosa* 'Dropmore Fernleaf', not patented, as the female, or seed, parent with *Sambucus racemosa* 'Sutherland Gold', not patented, as the male, or pollen, parent. The new *Sambucus* plant was discovered and selected by the Inventor in May, 2009 as a single flowering plant within the progeny of the stated cross-pollination in a controlled environment in Grand Haven, Mich.

Asexual reproduction of the new *Sambucus* plant by softwood cuttings in a controlled environment in Grand Haven, Mich. since June, 2009 has shown that the unique features of this new *Sambucus* plant are stable and reproduced true to type in successive generations of asexual reproduction.

SUMMARY OF THE INVENTION

Plants of the new *Sambucus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNSRD4'.

These characteristics in combination distinguish 'SMNSRD4' as a new and distinct *Sambucus* plant:

1. Compact, upright to outwardly spreading and mounded plant habit.
2. Vigorous growth habit.
3. Freely branching habit; dense and bushy habit.
4. Finely-dissected leaves that are bright yellow green in the spring and/or under full sunlight conditions and yellow green in the late summer and/or under partial shade conditions.
5. Leaves that resist sun scalding.
6. Good garden performance.

Plants of the new *Sambucus* can be compared to plants of the female parent, 'Dropmore Fernleaf'. Plants of the new *Sambucus* differ from plants of 'Dropmore Fernleaf' in the following characteristics:

1. Plants of the new *Sambucus* are more compact than plants of 'Dropmore Fernleaf'.
2. In the spring and/or under full sunlight conditions, leaves of plants of the new *Sambucus* are bright yellow green in color whereas leaves of plants of 'Dropmore Fernleaf' are green in color.

Plants of the new *Sambucus* can be compared to plants of the male parent, 'Sutherland Gold'. Plants of the new *Sambucus* differ from plants of 'Sutherland Gold' in the following characteristics:

1. Plants of the new *Sambucus* are more compact than plants of 'Sutherland Gold'.
2. Leaves of plants of the new *Sambucus* are more finely dissected than leaves of plants of 'Sutherland Gold'.
3. Under full sunlight conditions, leaves of plants of the new *Sambucus* resist sun scalding whereas leaves of plants of 'Sutherland Gold' are not resistant to sun scalding.

Plants of the new *Sambucus* can be compared to plants of the *Sambucus nigra* 'Eiffel 1', disclosed in U.S. Plant Pat. No.

23,633. Plants of the new *Sambucus* differ from plants of 'Eiffel 1' in the following characteristics:

1. Plants of the new *Sambucus* are upright to outwardly spreading and mounding whereas plants of 'Eiffel 1' are columnar in shape.
2. Leaves of plants of the new *Sambucus* are bright yellow green to yellow green in color whereas leaves of plants of 'Eiffel 1' are dark purple in color.

BRIEF DESCRIPTION OF THE PHOTOGRAPHS

The accompanying colored photographs illustrate the overall appearance of the new *Sambucus* plant showing the colors as true as it is reasonably possible to obtain in colored reproductions of this type. Colors in the photographs may differ slightly from the color values cited in the detailed botanical description which accurately describe the colors of the new *Sambucus* plant.

The photograph on the first sheet is a side perspective view of a typical plant of 'SMNSRD4' grown in an outdoor nursery under full sunlight conditions.

The photograph on the second sheet is a side perspective view of a typical plant of 'SMNSRD4' grown in an outdoor nursery under partial shade conditions.

DETAILED BOTANICAL DESCRIPTION

The aforementioned photographs and following observations, measurements and values describe plants grown during the spring and summer in three-liter containers and ground beds in an outdoor nursery in Grand Haven, Mich. and under cultural practices typical of commercial production. Plants were three years old when the photographs and the description were taken. In the description, color references are made to The Royal Horticultural Society Colour Chart, 1995 Edition, except where general terms of ordinary dictionary significance are used.

Botanical classification: *Sambucus racemosa* 'SMNSRD4'.

Parentage:

*Female, or seed, parent.*—*Sambucus racemosa* 'Dropmore Fernleaf', not patented.

*Male, or pollen, parent.*—*Sambucus racemosa* 'Sutherland Gold', not patented.

Propagation:

*Type*.—By softwood cuttings.

*Time to initiate roots, summer*.—About 18 days at temperatures about 27° C.

*Time to produce a rooted young plant, summer*.—About 60 days at temperatures about 27° C.

*Root description*.—Fine to thick; white and brown in color.

*Rooting habit*.—Freely branching; dense.

Plant description:

*Plant and growth habit*.—Perennial shrub; compact, upright to outwardly spreading and mounded plant habit; vigorous growth habit.

*Branching habit*.—Freely branching habit with about ten lateral branches developing per plant; pinching enhances lateral branch development.

*Plant height*.—About 1.25 meters.

*Plant diameter* (*area of spread*).—About 2.5 meters.

*Lateral branches*.—Length: About 20 cm. Diameter: About 6 mm. Internode length: About 6 cm. Texture: Smooth, glabrous. Aspect: Erect to about 30° from vertical. Strength: Strong. Color, developing: Close to 145A. Color, developed: Close to 199B.

Leaf description:

*Arrangement*.—Opposite; compound with five to seven leaflets per leaf.

*Leaflet length*.—About 7 cm to 12 cm.

*Leaflet width*.—About 3 cm to 11 cm.

*Leaflet shape*.—Oblanceolate to lanceolate, deeply dissected.

*Leaflet apex*.—Acute.

*Leaflet base*.—Cuneate to obtuse.

*Leaflet margin*.—Deeply dissected.

*Texture, upper and lower surfaces*.—Smooth, glabrous.

*Venation pattern*.—Pinnate.

*Color, spring and/or under full sunlight conditions*.—Developing leaves, upper and lower surfaces: Close to 4A tinged with close to 56A. Fully expanded leaves, upper surface: Close to 151A; venation, close to 151A. Fully expanded leaves, lower surface: Close to 145B; venation, close to 145B.

*Color, late summer and/or under partial shade conditions*.—Developing leaves, upper and lower surfaces: Close to 150A. Fully expanded leaves, upper surface: Close to 146C; venation, close to 146C. Fully expanded leaves, lower surface: Close to 139C; venation, close to 139C.

*Petioles*.—Length: About 4 cm. Diameter: About 3 mm. Texture, upper and lower surfaces: Smooth, glabrous. Color, upper and lower surfaces, spring and/or under full sunlight conditions: Close to 151A. Color, upper and lower surfaces, late summer and/or under partial shade conditions: Close to 146C.

Inflorescence & flower description:

*Flower appearance and arrangement*.—Single rotate flowers arranged on dense terminal paniculate cymes; freely flowering habit with usually about 96 flowers developing per inflorescence; flowers face upright, outwardly to downward depending on position on the head.

*Natural flowering season*.—Plants begin flowering in early May in Michigan.

*Flower longevity*.—Flowers last about two weeks on the plant; flowers not persistent.

*Fragrance*.—None detected.

*Inflorescence height*.—About 7 cm.

*Inflorescence diameter*.—About 6 cm.

*Flower diameter*.—About 7 mm.

*Flower length* (*height*).—About 6 cm.

*Flower buds*.—Length: About 2 mm. Diameter: About 2 mm. Shape: Globose. Color: Close to 145B to 145C.

*Petals*.—Quantity and arrangement: Five petals in a single whorl. Length: About 3.5 mm. Width: About 2 mm. Shape: Lanceolate, reflexed. Apex: Obtuse. Margin: Entire. Texture, upper and lower surfaces: Smooth, glabrous; waxy. Color: When opening and fully opened, upper surface: Close to 145C; color becoming closer to 177B with development. When opening and fully opened, lower surface: Close to 145B; color becoming closer to 177B with development.

*Sepals*.—Quantity and arrangement: Five sepals in a single whorl. Length: About 1 mm. Width: About 1 mm. Shape: Lanceolate. Apex: Acute. Margin: Entire. Texture, upper and lower surfaces: Smooth, glabrous. Color: When opening, upper and lower surfaces: Close to 145B. Fully opened, upper and lower surfaces: Close to 145A.

*Peduncles*.—Length: About 4 cm. Diameter: About 2 mm. Strength: Strong. Aspect: Mostly upright. Texture: Smooth, glabrous. Color: Close to 145A.

*Pedicels*.—Length: About 2.5 mm. Diameter: About 1 mm. Strength: Strong. Aspect: Upright to horizontal depending on position on the inflorescence. Texture: Smooth, glabrous. Color: Close to 145A.

*Reproductive organs*.—Androecium: Quantity per flower: About five. Anther length: About 2.5 mm. Anther shape: Oblong. Anther color: Close to 145B. Amount of pollen: Moderate. Pollen color: Close to 150D. Gynoecium: Quantity per flower: One to three-parted. Pistil length: About 2 mm. Style length: About 1.8 mm. Style color: Close to 145C. Stigma appearance: Globular, three-lobed. Stigma color: Close to 145C. Ovary color: Close to 145C.

*Fruits and seeds*.—Fruit and seed development have not been observed on plants of the new *Sambucus*.

Garden performance: Plants of the new *Hydrangea* have been observed to have good garden performance by exhibiting good tolerance to rain and wind; to be resistant to sun scalding; and to tolerate temperatures ranging from about −32° C. to about 36° C.

Pathogen & pest resistance: Plants of the new *Sambucus* have not been observed to be resistant to pathogens and pests common to *Sambucus* plants.

It is claimed:

1. A new and distinct *Sambucus* plant named 'SMNSRD4' as illustrated and described.

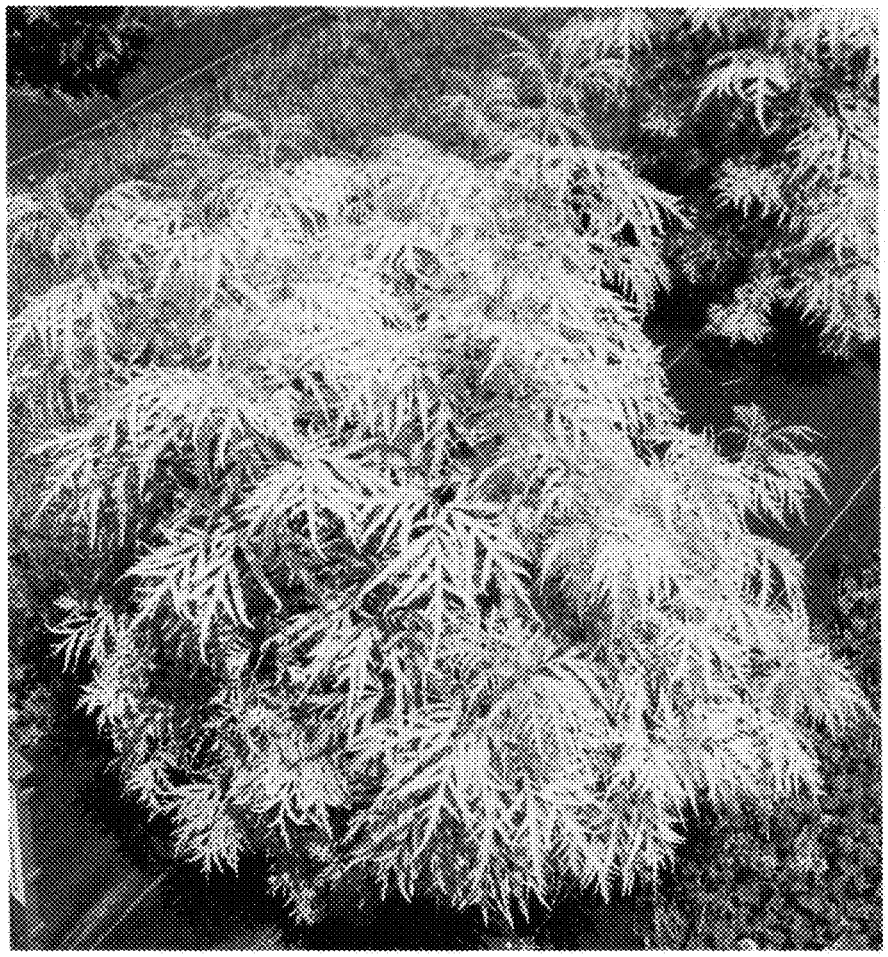

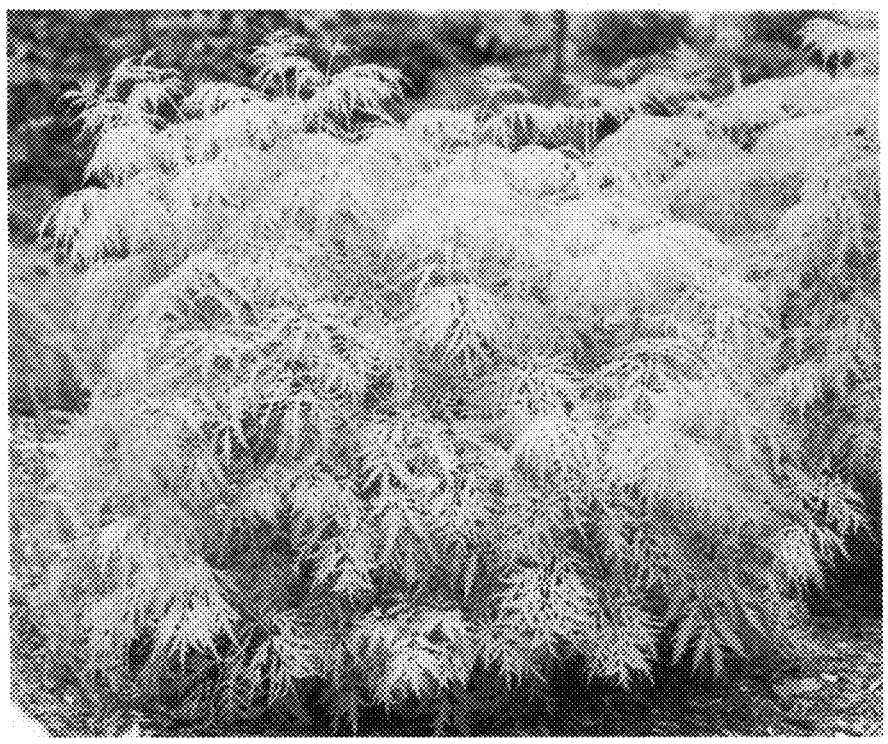

* * * * *